(12) United States Patent
Malver et al.

(10) Patent No.: US 6,623,616 B1
(45) Date of Patent: Sep. 23, 2003

(54) CORROSIVE ENVIRONMENT MONITOR AND METHODS REGARDING SAME

(75) Inventors: Frederick S. Malver, New Brighton, MN (US); Paul L. Gibson, Andover, MN (US); Ronald H. Jiracek, Maple Grove, MN (US); Darryl G. Busch, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/560,257

(22) Filed: Apr. 26, 2000

(51) Int. Cl.[7] ............................................. G01N 27/403
(52) U.S. Cl. ................. 205/775.5; 205/776.5; 205/777; 205/778.5; 205/787; 204/404
(58) Field of Search ................. 204/404, 433, 204/416; 205/775.5, 776, 776.5, 777, 787.5, 778.5; 73/86

(56) References Cited

U.S. PATENT DOCUMENTS 5,437,773 A * 8/1995 Glass et al. .................. 204/404
5,549,803 A   8/1996 Schoess et al. ............. 204/404
5,676,820 A * 10/1997 Wang et al. ............. 205/777.5

OTHER PUBLICATIONS

Miller et al "Preventing Aircraft Corrosion by Predictive Corrosion Modeling", AFWAL–TR–87–4139, 1987 (complete document).*

Li et al "Mathematical Models for Dependence of Atmospheric Corrosion on Environment Factors and Prediction of Atmospheric Corrosion", ISTIC–Technical Report 95,051, 1995, month unavailable.*

CAS Abstract for Miller et al "Preventing Aircraft Corrosion by Predictive Corrosion Modeling", AFWAL–TR–87–4139, 1987, month unavailable.*

England et al "Applications of a Real–Time Electronic Contact Corrosion Monitor", Adv. Instrum. Control (1991), vol. 46, pp. 929–955, month unavailable.*

Office of Naval Research, "Intelligent Corrosivity Sensor [ICS]", News Press Release, System Information and Operating Manual 9 pgs., (Feb. 1, 1999) and related article.

* cited by examiner

Primary Examiner—Nam Nguyen
Assistant Examiner—Kaj K. Olsen
(74) Attorney, Agent, or Firm—Kris T. Fredrick

(57) ABSTRACT

A monitoring method and system to monitor an environment in which an object is located includes monitoring one or more environmental factors associated with corrosion of materials in the environment. Thereafter, an exposure index representative of cumulative exposure of the object to the one or more environmental factors is determined. For example, such environmental factors may include chloride ion concentration, pH level, humidity, and temperature.

32 Claims, 5 Drawing Sheets

FIGURE 5
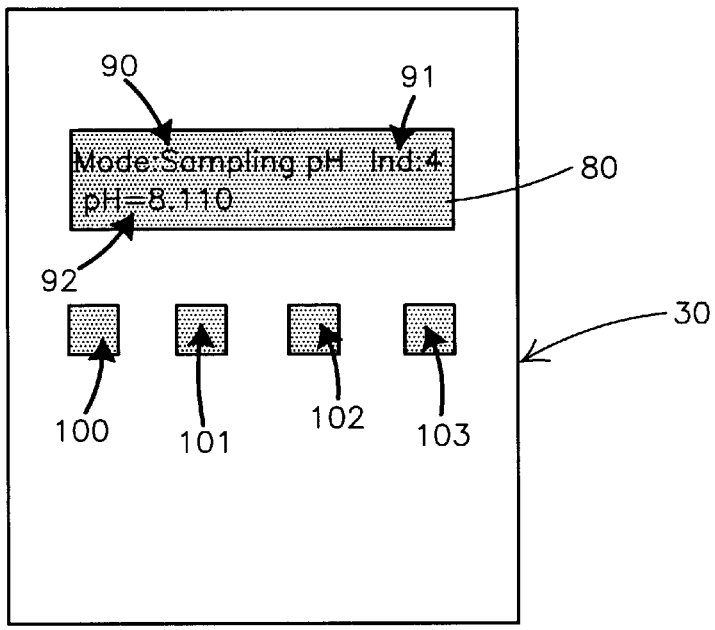
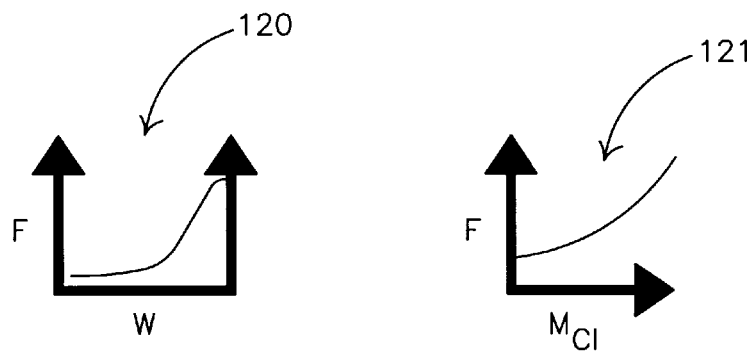
FIGURE 6A  FIGURE 6B
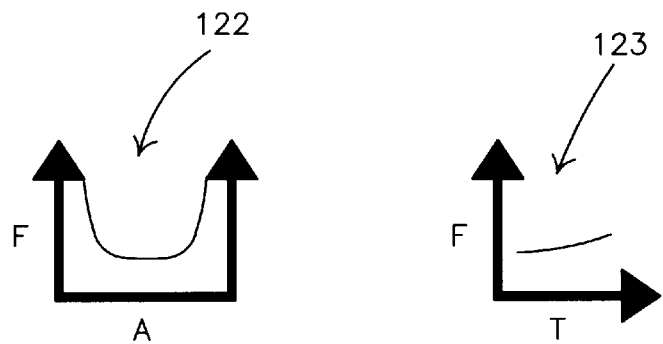
FIGURE 6C  FIGURE 6D

CORROSIVE ENVIRONMENT MONITOR AND METHODS REGARDING SAME

STATEMENT OF GOVERNMENT RIGHTS

The present invention was made with government support from the U.S. Army Aviation, Applied Technology Directorate under Contract No. DAAH10-99-2-0004. The Government has certain rights in this invention.

FIELD OF THE INVENTION

The present invention is generally related to monitoring systems and methods. More particularly, the present invention pertains to monitoring in corrosive environments.

BACKGROUND OF THE INVENTION

Metal-containing structures are vulnerable to the attack of corrosion. Defenses against corrosion are many and vary in effectiveness. Ultimately, inspections, some of which can be very costly, are typically called for to monitor the progress of corrosion. These inspections are usually scheduled on an established time basis. For example, with respect to aircraft structure, regularly scheduled calendar inspections may be performed (e.g., daily inspections may be performed through visual checks), inspections may be performed based on operating time, and inspections may be based on use of the aircraft and the conditions to which the aircraft has been subjected (e.g., freshwater or saltwater landings, operation in muddy or swampy terrain, washing or after heavy rains, etc.).

Corrosion typically occurs in regions that are subjected to excess moisture or wetted by other fluids. For example, in the fuselage of an aircraft, these areas may include the fuel shelf areas, wheel well shelves/back walls in various aircraft, doors including cargo access and landing gear doors, floors of cargo bays, etc.

Various existing non-destructive inspection methods are available to detect corrosion. These detection methods include visual tests, tap test, electrical resistance probing, electrochemical analysis, ultrasonic, eddy current, x-ray radiography, and acoustic emission with heat.

Further, various corrosion sensors are available. For example, one such sensor is described in U.S. Pat. No. 5,549,803 to Schoess et al., entitled "Smart Fastener," issued Aug. 27, 1996. However, although various corrosion sensors are available, such corrosion sensors typically detect corrosion only after it is already occurring. As such, because corrosion is already occurring, preventive action is more difficult to implement.

Generally, preventive measures are indicated as being necessary by inspections as described above, e.g., daily inspections, calendar-based inspections, etc. However, such maintenance inspections are costly. Therefore, it is desirable to reduce the number of inspections or provide for more optimized time periods between inspection events. For example, in mild corrosive environments, abbreviated inspections may be carried out every 90 days, with in-depth inspections being carried out every 180 days. In comparison, in more severe corrosive environments, such abbreviated inspections may be carried out every 15 days, with in-depth inspections being carried out every 30 days.

However, it is difficult to judge what environment conditions will be within a certain time period, even within a particular geographical location. As such, for example, scheduling in-depth inspections every 30 days in geographical areas characterized by severe corrosive environments even during time periods when such corrosive environmental conditions are not occurring is inefficient. Therefore, calendar-based inspections even when scheduled based on the generalized corrosive environmental conditions of certain geographical regions is inadequate from a cost efficiency standpoint.

SUMMARY OF THE INVENTION

The present invention provides a monitoring apparatus and method to monitor the presence of corrosive agents in a spatial volume, e.g., the space under the cargo bay floor of an aircraft. The monitor generates an exposure index, e.g., an index which is intended to provide a condition-based metric that indicates when a corrosion inspection should be performed. The monitoring apparatus and method can be used for various purposes, including, but not limited to, scheduling of inspections on a condition basis as opposed to calendar-based inspection.

A monitoring method according to the present invention for monitoring an environment in which an object is located includes monitoring one or more environmental factors (e.g., chloride ion concentration, pH, humidity, etc.) associated with corrosion of materials in the environment. An exposure index representative of cumulative exposure of the object to the one or more environmental factors is then determined based on the monitored environmental factors.

In one embodiment of the method, the exposure index is indicated to a user, such as by displaying the exposure index, setting off an alarm or LED indicator, etc. Further, such an exposure index may be continuously updated and/or displayed. Yet further, in other embodiments of the method, data representative of the monitored environmental factors is recorded.

In yet another embodiment of the method, the object may be inspected as a function of the exposure index. Such inspection is representative of a condition-based inspection as opposed to a calendar-based inspection.

In addition, in various embodiments of the method, the one or more environmental factors associated with corrosion of materials includes at least one of chloride ion concentration, pH, temperature, and humidity. Further, a measured free potential of a sample material representative of a material of which the object is formed may be measured. The measured free potential may be used to verify the exposure index.

A monitoring apparatus for monitoring an environment in which an object is located is also described according to the present invention. Such a monitoring apparatus includes one or more sensors. Each sensor is operable to detect the presence of at least one environmental factor associated with corrosion of materials and provide a sensor signal representative of the detected environmental factor. A processing unit is operable to receive the sensor signals generated by the one or more sensors. The processing unit determines an exposure index representative of cumulative exposure of the object to the one or more environmental factors as a function of the received sensor signals.

In one embodiment of the apparatus, an indication device is used to provide a user with an indication of the exposure index, e.g., the index is displayed for a user. Further, the apparatus may include memory to store data representative of at least one of the exposure index and/or data representative of the sensor signals. Preferably, the indication device continuously updates the exposure index.

In other embodiments of the apparatus, the sensors may include at least one of a chloride ion concentration sensor, a pH sensor, a humidity sensor, a clocking device for use in determining time of wetness, a sensor to measure free potential of a sample material (e.g., a material of which the object is formed) positioned in the environment.

Another monitoring method for monitoring an environment in which an object is located is also described. The monitoring method includes monitoring at least chloride ion concentration and pH in the environment in which the object is located. An exposure index representative of cumulative exposure of the object to at least chloride ion concentration and pH is determined.

Preferably, in addition to monitoring chloride ion concentration and pH in the environment, humidity and temperature is monitored and time of wetness in the environment is also determined. Based on such environmental factors, an exposure index is determined.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIG. 5 is a block diagram of one illustrative embodiment of an indication device, e.g., display and function buttons, of a user interface such as that shown in FIG. 4.

FIGS. 6A–6D are graphical representations for use in describing the determination of an exposure index for the corrosive environment monitor as generally shown in FIG. 1.

DETAILED DESCRIPTION OF THE EMBODIMENTS

Figure 1:
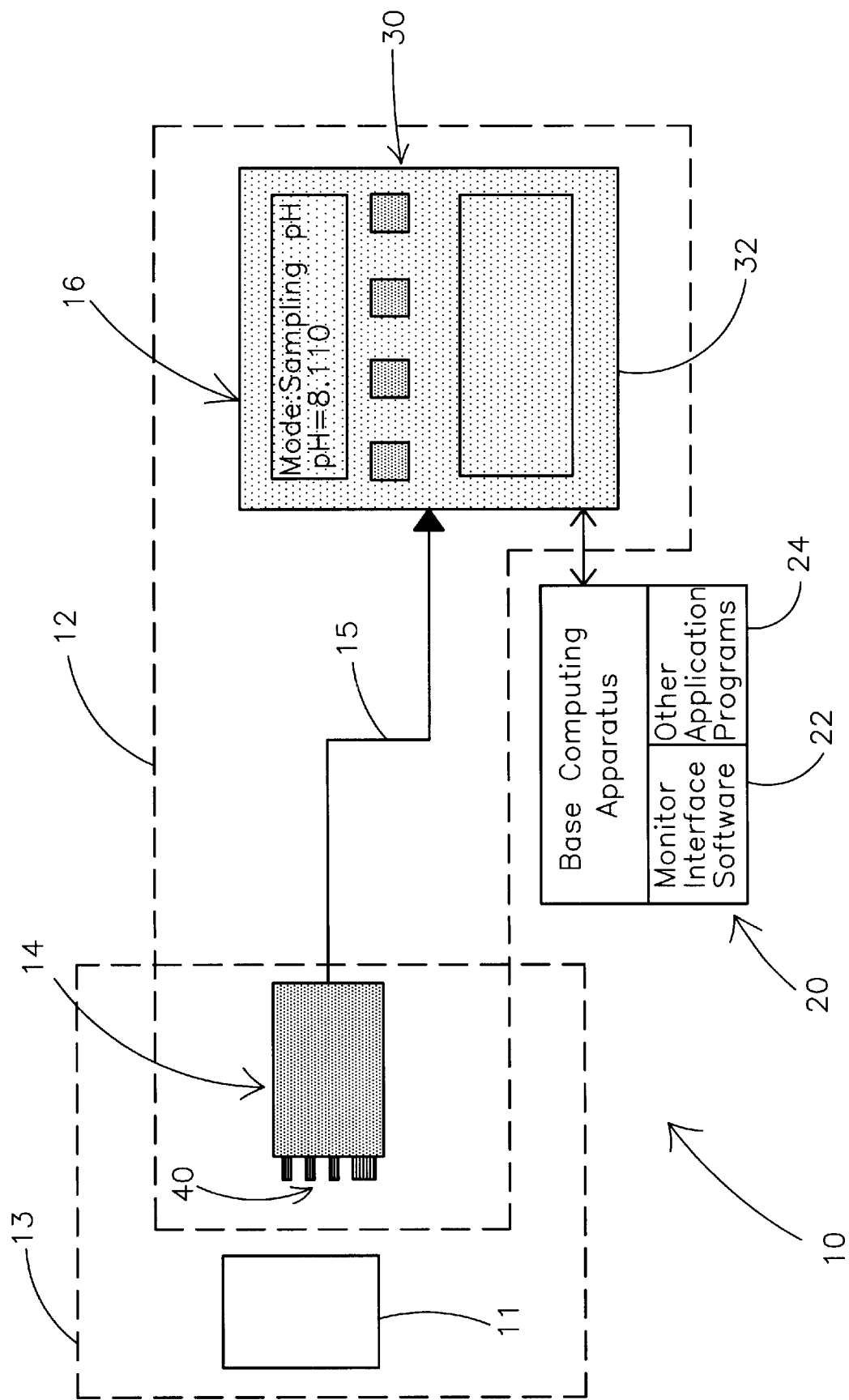
FIG. 1 is a block diagram of a monitoring system including a corrosive environment monitor according to the present invention.

FIG. 1 shows a block diagram of a monitoring system 10 including a corrosive environment monitor 12 according to the present invention. The corrosive environment monitor 12 monitors one or more environmental factors associated with corrosion of an object 11 in an environment 13 in which the object 11 is located. The corrosive environment monitor 12 determines an exposure index representative of cumulative exposure of the object 11 to one or more environmental factors being monitored. For example, in one embodiment of the corrosive environment monitor 12, the monitor 12 is designed to monitor the presence of corrosive agents in a spatial volume, such as a space under the cargo bay floor of an aircraft, e.g., a helicopter. However, the corrosive environment monitor 12 may be used for monitoring any environment 13 for which the present invention provides benefit. Preferably, the corrosive environment monitor 12 is used to monitor corrosive environmental factors in hidden and/or inaccessible locations. For example, the monitor 12 may be used to monitor the ionized constituents of corrosion causing fluids trapped in such locations. Further, for example, the exposure index determined as a finction of the monitored environmental factors may provide a condition-based metric that indicates when a corrosion inspection should be performed. Such a condition-based metric may be considered analogous to a car's odometer monitoring mileage to indicate the need for maintenance, e.g., an oil change, etc.

Preferably, condition-based scheduling of inspections of object 11 are performed based on the exposure index. However, such scheduling of inspections may be based solely on the exposure index or may be based on a combination of a calendar-based inspection process in combination with a condition-based process as described herein. For example, calendar-based inspections, e.g., an in-depth inspection every 90 days for a particular geographical area in which the object 11 is used, may be used as the underlying scheduling premise with such underlying premise being optimized through the use of the exposure index.

Although the present invention focuses on the use of the exposure index for scheduling of maintenance checks regarding corrosion of object 11, the present invention is not to be limited to use of the exposure index in only such limited circumstances. Other health and usage applications may utilize such an exposure index in beneficial manners. For example, such a corrosive environment monitor may be used for other purposes such as transport vehicles, ships, containers, or structures in general.

Preferably, according to the present invention, object 11 may be any structure vulnerable to attack of corrosion. For example, such problems may be associated with shipping containers, trucks, aircraft, ships, any sort of container vessels, and particularly applicable to objects having moisture collection problems. However, the present invention is not limited to any of the specific objects 11 listed herein but may be applicable to any number of objects.

The monitoring system 10 includes base computing apparatus 20 which may be used to program corrosive environment monitor 12 as further described below. The corrosive environment monitor 12 as shown in FIG. 1 includes a sensor module 14 and an electronic support module 16 interconnected by connection device 15, e.g., shielded cables, wireless interconnection, or any other electrical coupling apparatus.

The sensor module 14 contains one or more sensors 40 for use in sensing one or more environmental factors, preferably associated with corrosion of materials in the environment 13. The one or more sensors 40 may include any type of sensor operable to detect the presence of at least one environmental factor, preferably an environmental factor associated with the corrosion of materials. Preferably, the sensor provides a sensor signal representative of the detected environmental factor, e.g., representative of ion concentration, humidity, temperature, etc. For example, the one or more sensors 40 may include a chloride ion sensor, a pH sensor, a humidity sensor, a temperature sensor, a flow sensor, a pressure sensor, other ion-specific sensors, or any other sensor operable to provide a sensor signal to electronic support module 16 that may be beneficial in monitoring according to the present invention. Further, the one or more sensors 40 may include other types of sensors not representative of environmental factors such as a free potential electrode constructed of a specific sample material, e.g., metal, being monitored for corrosion, e.g., a material that forms at least a part of the object 11. In other words, the free potential electrode may serve as a reference to monitor corrosive activity occurring upon a sample piece of the same metal which forms at least a part of object 11 which is being monitored. One skilled in the art will recognize that any number of sensors may be used according to the present invention and that the list as provided herein is only representative of the types of sensors which can be utilized.

Preferably, one or more of the sensors 40 are commercial off-the-shelf sensors which can be easily replaced by interchangeable sensor types within sensor module 14. For example, interchangeable free potential electrodes may allow the corrosive environment monitor 12 to be easily modified for use in monitoring different types of materials and objects.

Electronic support module 16 includes data processing unit 32 for receiving sensor signals via interconnection 15. The electronic support module 16 controls the overall corrosive environment monitor 12. The data processing unit 32 receives the sensor signals and operates upon such signals to provide an exposure index and/or record such an exposure index and other data represented by the sensor signals. Further, as shown in FIG. 1, electronic support module 16 further includes a user interface 30 which provides information to a user regarding data resulting from analysis performed by data processing unit 32. For example, the user interface 30 may provide various functionality including, but clearly not limited to, a display of exposure index, a display of various data points associated with signals received from the one or more sensors 40, an alarm function or an LED indication to a user if one or more predetermined limits are met (e.g., exposure index exceeds a certain threshold), or any other user interface components which may provide benefit to a user.

Preferably, the data processing unit 32 includes an analog-to-digital converter and a processor for input/output control and data analysis. Preferably, the data analysis determines an exposure index representative of cumulative exposure of the object 11 to one or more environmental factors as a function of the received sensor signals. The exposure index provides an absolute measure of the cumulative exposure of object 11 to corrosive environmental factors. Such an exposure index provides an indication of the potential corrosion activity for the object 11 being monitored. This measure of cumulative exposure may be used to schedule corrosion inspections as previously described herein, and may be used to effectively replace and/or supplement a calendar-based inspection process for the object 11. The integral display and absolute exposure measurement allow the corrosive environment monitor 12 to essentially function as a corrosion dosimeter. In other words, the corrosion dosimeter can be used to schedule corrosion inspections on a condition basis.

Preferably, the corrosive environment monitor 12 includes separated sensor module 14 and electronic support module 16 interconnected by connection apparatus 15. However, the corrosive environment monitor 12 may include an integrated sensor module 14 and electronic support module 16. As such, the integrated modules would form a single device. However, preferably the sensor module 14 and electronic support module 16 are separate modules which communicate via connection apparatus 15 such that the sensor module 14 can be positioned in an inaccessible area and the electronic support module 16 including user interface 30 can be positioned where users can view and interact therewith.

Base computer apparatus 20 of monitoring system 10 is preferably a processor-based system, such as a 486 or larger central processing unit-based computer. Preferably, the base computer apparatus includes a PCMCIA card slot and sufficient memory and hard drive space to perform the requirements according to the present invention. The base computer apparatus 20 preferably provides a user-friendly graphical interface to the corrosive environment monitor 12 to provide programming or coding thereof as desired for a particular application. For example, the base computer apparatus 20 includes monitor interface software 22 which may allow a user to program various data collection parameters for the corrosive environment monitor 12 for the various sensors being used in the monitoring process. In other words, for example, parameters such as the sampling interval for the one or more sensors 40 may be set via base computer apparatus 20 or the computer apparatus may be used to modify other aspects of corrosive environment monitor 12 such as the desired algorithms for computing the dose exposure index.

Further, for example, base computer apparatus 20 may include other application programs utilized in the downloading of data from memory of the electronic support module 16 and operation thereon. For example, data with regard to one or more of the environmental factors detected by the one or more sensors 40 may be downloaded from sensor electronic support module 16 and operated upon by other application programs 24 to provide print-outs and/or graphs representative of the information obtained from the one or more sensors 40. Further, such application programs 24 may operate upon exposure index values generated by the electronic support module 16 and downloaded to the base computer apparatus 20. One skilled in the art will recognize that any processor-based system may carry out operation on such data and/or may be used to program the corrosive environment monitor 12. The present invention is not limited to any particular processor-based system or peripheral devices used therewith.

FIGS. 2–5 show various block diagrams of illustrative embodiments of certain components of the corrosive environment monitor 12 as generally shown in FIG. 1. Such illustrative embodiments of the various components may be used together in a combined unit to form a corrosive environment monitor or various components shown in the figures may be used in combination with other components of an equivalent nature to form a corrosive environment monitor 12 as generally shown in FIG. 1. Preferably, the following-described FIGS. 2–5 provide an electrochemical corrosive environment monitor that measures and stores information on environmental factors conducive to corrosion. Although various environmental factors may contribute and may be monitored according to the present invention, in the embodiment described with reference to such figures, the environmental factors considered are chloride ion concentration, pH, humidity, and temperature. From such factors, the corrosive environment monitor calculates a dose exposure index, e.g., a dosimeter value. In such a manner, corrosion inspections can be performed based on the accumulated exposure level measured by the dose exposure index. For example, an aircraft may be inspected based on the exposure index. The corrosive environment monitor continuously operates independent of operational status of the object 11 being monitored, e.g., the operational status of an aircraft. The index value to be determined by the monitor may be continuously updated and displayed such that maintenance personnel of the aircraft may read the index regularly to decide whether inspection is necessary.

The corrosive environment monitor detailed in the illustrative diagrams of FIGS. 2–5, excluding the free potential electrode, is an environment monitor, not a corrosion sensor.

It detects corrosion-causing conditions to prompt corrosion prevention actions, e.g., condition-based inspections.

Figure 2:
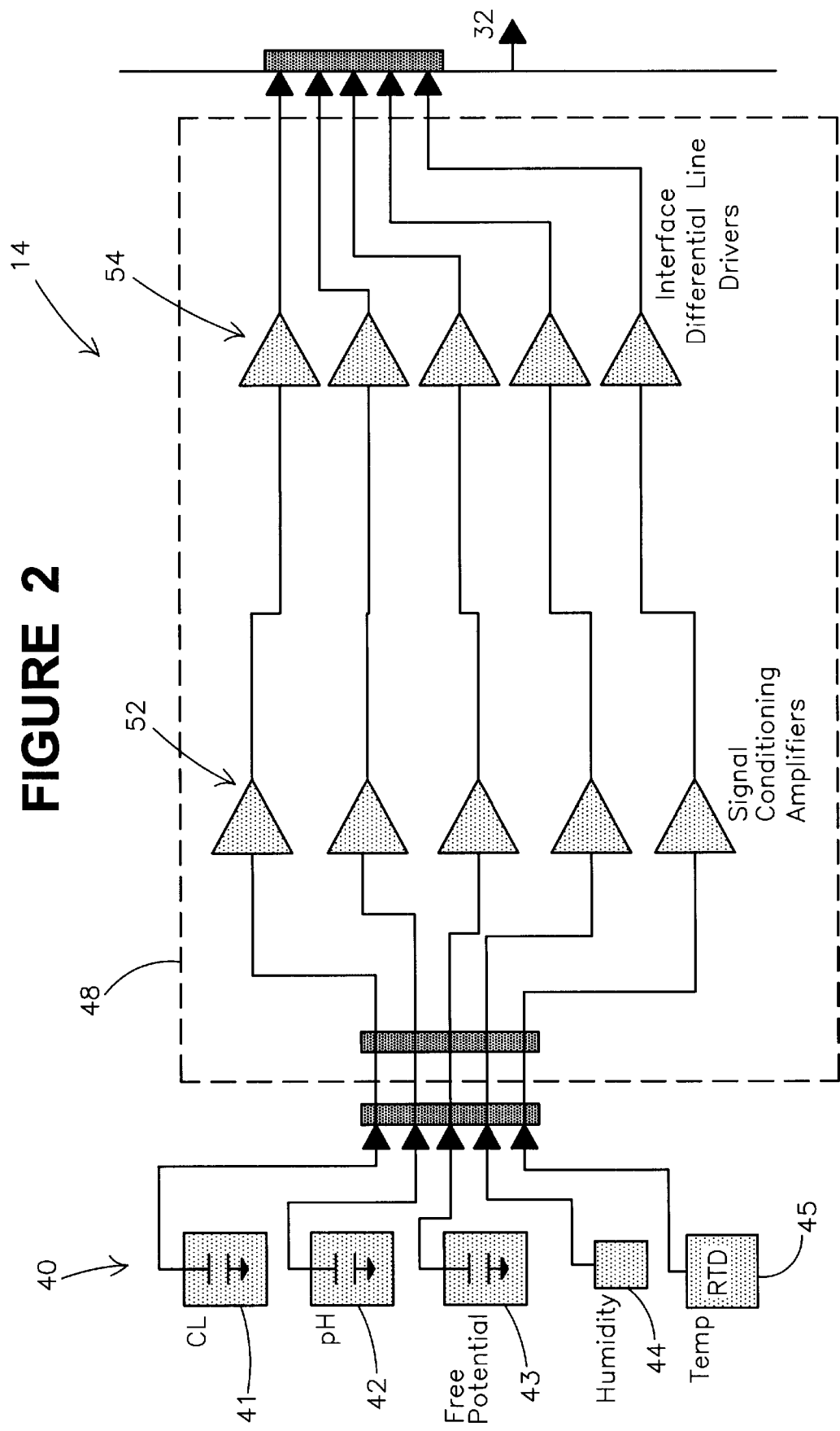
FIG. 2 is a block diagram of one illustrative embodiment of a sensor module of the corrosive environment monitor as generally shown in FIG. 1.

FIG. 2 shows a block diagram of an illustrative embodiment of a sensor module 14 to be used in a corrosive environment monitor 12. The sensor module 14 shown in FIG. 2 includes the one or more sensors 40 and sensor module interface circuitry 48. The one or more sensors 40 include environmental factor sensors 41–42 and 44–45. Such sensors include chloride ion concentration sensor 41, pH sensor 42, humidity sensor 44, and temperature sensor 45. The chloride ion concentration sensor 41 may include any sensor for providing a sensor signal representative of chloride ion concentration such as, for example, a commercially off-the-shelf sensor available under the trade designation of detectION, Ion Selective Electrodes available from Nico Scientific. Likewise, pH sensor 42 may include any sensor operable to provide a sensor signal representative of pH in the environment and may include, for example, a commercially off-the-shelf sensor available under the trade designation of Electrochemical Sensors available from SenTek Corporation. In addition, humidity sensor 44 includes any sensor operable for providing a sensor signal representative of humidity and may include, for example, a commercially off-the-shelf sensor available under the trade designation of TRH-100 available from Pace Scientific, Inc. Further, temperature sensor 45 may include any sensor for sensing temperature, such as, for example, a commercially off-the-shelf sensor available under the trade designation of TRH-100 available from Pace Scientific, Inc.

The one or more sensors 40 may also include a free potential electrode 43 as previously described with reference to FIG. 1, which serves as a reference to directly monitor the corrosive activity upon a sample piece of a metal of the same nature as that being monitored. For example, if object 11 is formed at least in part of aluminum, then a sample piece of aluminum is used and a supplemental measurement, i.e., free potential of aluminum, is taken to provide a measure of the actual corrosion on the sample electrode formed of aluminum.

The sensor signal provided by temperature sensor 45 may be used in determination of an exposure index representative of the corrosive environment in the same manner as the chloride ion concentration, pH, and humidity as further described below. However, the temperature sensor 45 which provides an output representative of temperature of the environment may be used by the data processing unit 32, as described with reference to FIG. 3, to correct the temperature dependency of the other sensors, such as the chloride ion concentration sensor, the pH sensor, and the humidity sensor 44. Many sensors require some correction for temperature fluctuation.

The reference electrode or free potential electrode 43 produces a signal representative of the actual corrosion on the sample piece of the metal being monitored. The signal provided by the free potential electrode may be used as a verification signal. For example, the verification signal may be used to verify the start of corrosive activity. Further, for example, such a signal may be used in the determination of or for weighing the impact of the other sensed environmental factors in determination of the exposure index as further described below.

Each of the one or more sensors 40 is driven to provide a signal of the respective factor it is measuring. Such signals are applied to respective signal conditioning amplifiers 52 for any necessary desired conditioning, e.g., gain, buffering, etc., and thereafter provided to a respective interface differential line driver 54 for application to data processing unit 32 shown and described with reference to FIG. 3.

Figure 3:
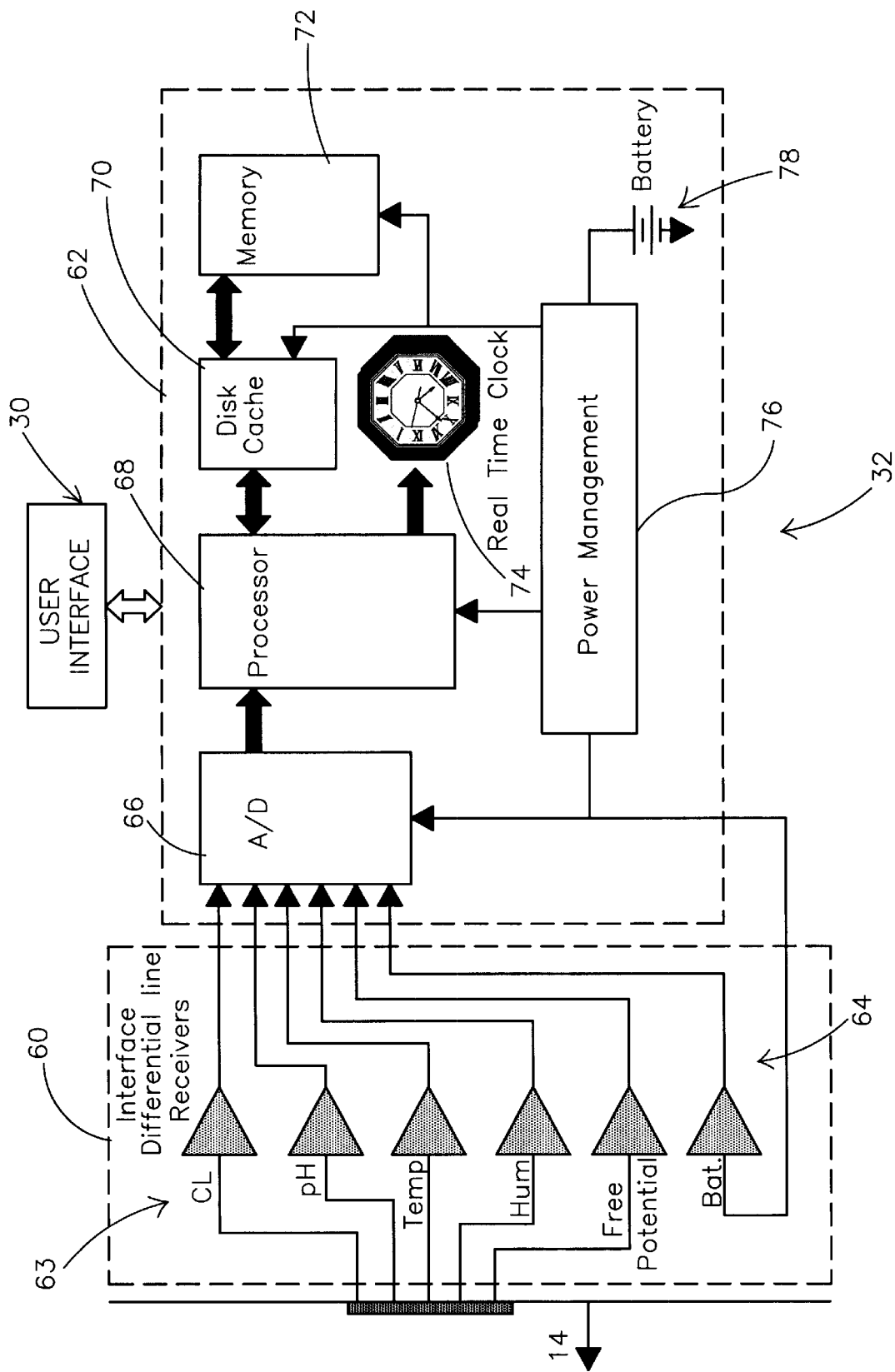
FIG. 3 is a block diagram of one illustrative embodiment of an electronic support module of the corrosive environment monitor as generally shown in FIG. 1.

Data processing unit 32, as illustratively shown in the block diagram of FIG. 3, generally provides for input/output control and data analysis. The data processing unit 32 includes a real-time clock 74 that controls the data sampling rate of the various sensors 41–45. The real-time clock 74 also is used to timestamp the data. Time-stamping the data is used for recording purposes with respect to each sensor. Such time-stamping is important with regard to the determination of the time of wetness with respect to determination of the effects of humidity on the exposure index. For example, time of wetness is determined with use of humidity sensor 44. By timestamping the data as the humidity sensor 44 is sampled, a time period length indicative of the time of a particular wetness, e.g., a level of humidity, can be recorded.

Data processing unit 32 of an electronics support module 16 includes monitoring and recording circuitry 62 and monitoring module interface circuitry 60. The monitoring module interface circuitry 60 receives respective sensor signals from sensor module 14 for the one or more sensors 40. Each of the respective signals from the one or more sensors 40 is received by a respective interface digital line receiver 63 and sampled under control of real-time clock 74 by analog-to-digital converter 66 of the monitoring and recording circuitry 62. The analog-to-digital converter 66 may be any analog-to-digital converter such as, for example, a 12-bit converter, an 8-bit converter, or any other appropriate size converter.

The monitoring and recording circuitry 62 further includes processor 68. The processor 68 may be any computing apparatus such as a microprocessor, e.g., a PIC 16C74 processor. The processor 68 operates upon the sampled data of the one or more sensors 40 to provide an exposure index representative of the cumulative exposure of the object 11 to the environmental factors being monitored. Preferably, firmware provides for calculation of the corrosion exposure index. Determination of the exposure index shall be described further below.

Data is stored in and retrieved from memory 72 under control of processor 68, via disk cache 70. For example, memory 72, such as a PCMCIA flash disk memory, may be available for uploading data to a base computer apparatus 20 such as that shown and described with reference to FIG. 1.

The various components of the system are powered under control of power management component 76 which provides adequate power from battery source 78. Various components may be used to distribute power in the system and conserve power as well. For example, amplifier 64 may be used to buffer power supplied to analog-to-digital converter 66 and is also used for providing a signal sampled for determining if battery power is low. Further, for example, the battery source 78 may be supplied by four AA batteries and the power management component 76 may be used to power down the unit in a sleep mode depending upon the use of the monitor 12.

In communication with the monitoring and recording circuitry 62 is user interface 30. The user interface 30, for example, may provide the user the ability to view information related to the corrosive environment monitor, e.g., real-time data of one or more of the sensors, the calculated exposure index, etc., and provide for user control of the functions being performed by the corrosive environment monitor 12.

Figure 4:
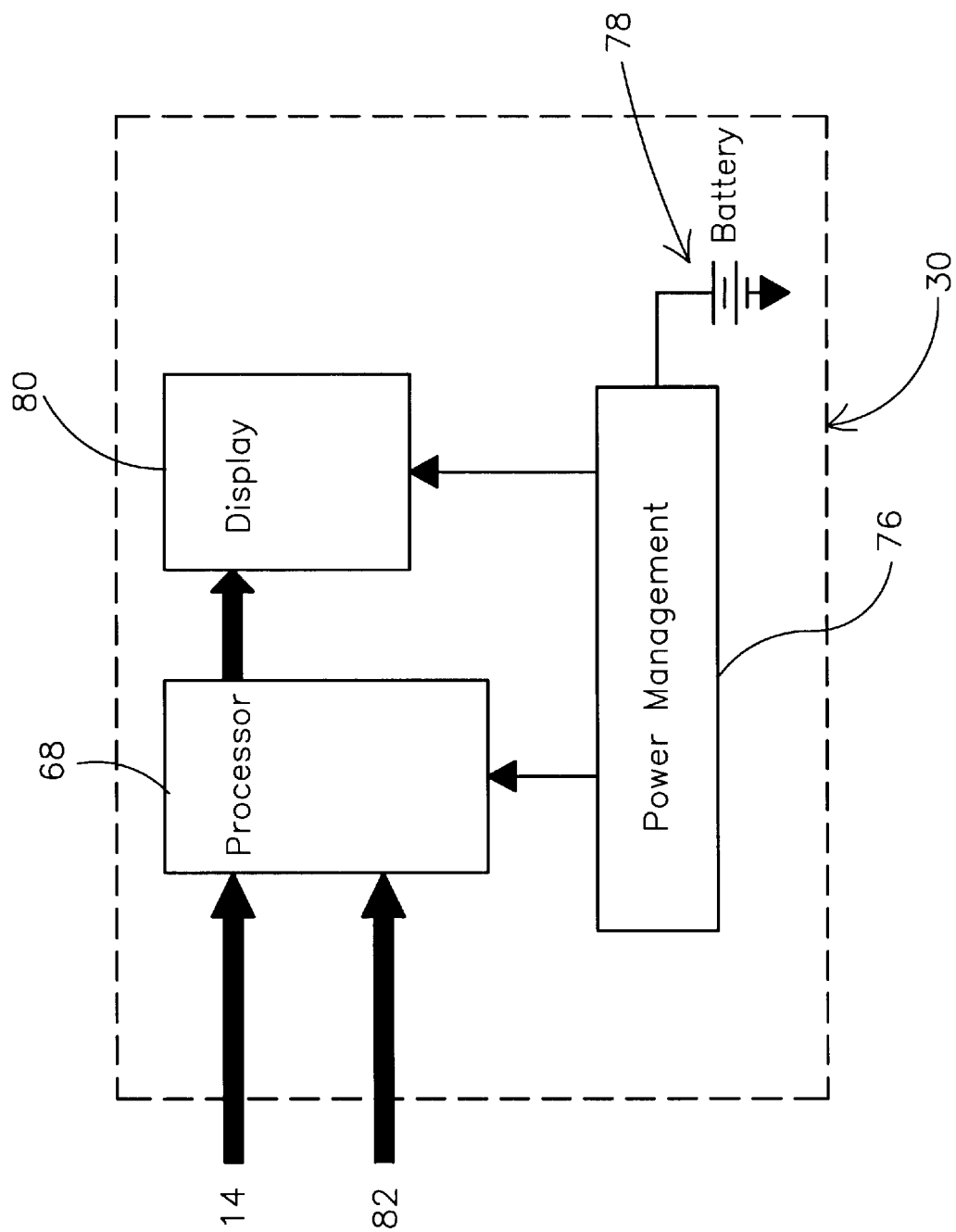
FIG. 4 is a block diagram of one illustrative embodiment of a user interface of the corrosive environment monitor as generally shown in FIG. 1.

One illustrative embodiment of a user interface 30 is shown and described with reference to FIG. 4. For example, the user interface 30 may include operation under control of processor 68 powered by power management system 76 receiving power to be distributed from battery source 78. In the embodiment of FIG. 4, the processor 68 receives input from sensor module 14, e.g., via analog-to-digital converter 66, and may be controlled by user activation or input devices 82, e.g., pushbuttons, a mouse, or any other type of user controllable activation devices. Using the user interface 30, various information can be displayed on display 80 under control of processor 68 and associated user input from user input devices 82.

One illustrative display 80 and user input device 82 is represented by the user interface 30 as shown and described with reference to FIG. 5. In FIG. 5, the user interface 30 includes an LCD display panel 80 for displaying various types of data, including, for example, function mode 90, exposure index 91, and sensor information 92. For example, the user interface 30 may include seven user-selectable functions via pushbuttons 100–103. For example, pushbutton 100 may be used as a function select button to select a function including one of a self test, a status of operation, real-time sample read-out of sensor data (e.g., pH, chloride ion concentration, temperature, humidity, and free potential). Pushbutton 101 may be used to execute the finction selected by finction select button 100. Further, pushbutton 102 may be used to provide backlighting on the LCD and pushbutton 103 may be an on/off switch for providing power to the LCD. As shown in FIG. 5, a real-time sample read-out of the pH sensor has been selected as the function as shown in finction mode region 90 of the display 80 with the pH being shown in the sample read-out data region 92 of the display 80. Likewise, an exposure index of 4 has been determined by the monitor 12 and is shown in exposure index region 91 of the display 80. One skilled in the art will recognize that various other user interfaces may be used with the monitor according to the present invention and that the present invention is not limited to any particular manner of interfacing with the user.

The generation of the exposure index (I) shall now be described with reference to FIGS. 6A–6D. The exposure index (I) provides a measure of the cumulative exposure of the object 11 to corrosive environmental factors. One or more factors may be used to determine the exposure index. Preferably, at least one of chloride ion concentration and pH is used to generate the exposure index. More preferably, both chloride ion concentration and pH are used to generate the exposure index, and even more preferably, chloride ion concentration, pH level, humidity, and temperature are all used to generate the exposure index. In other words, preferably, the exposure index $(I)=\int dt * f(W, M_{cl}, A, T)$, where W is equal to humidity (e.g., wetness); $M_{cl}$ is equal to chloride ion concentration; A is equal to acidity (pH), and T is equal to temperature.

FIG. 6A–6D summarizes the functional form for the development of the computation of the exposure index calculation. Graph 120 as shown in FIG. 6A relates humidity or wetness to the exposure index (I), graph 121 as shown in FIG. 6B relates the measured environmental factor of chloride ion concentration to exposure index (I), graph 122 as shown in FIG. 6C relates the environmental factor of pH level or acidity to the exposure index (I), and graph 123 as shown in FIG. 6D relates the environmental factor of temperature to the exposure index (I) determination. Various scaling or weighting parameters are determined using statistical analysis of data gathered from various situations in a calibration process to provide an exposure index calculation. As such, the exposure index calculation may vary depending upon the data gathered, and no particular exposure index function is explicitly stated herein. The exposure index function is developed using mathematical models that are determined using a combination of "first principles" chemistry concepts and empirical laboratory and testing data.

As shown in FIG. 6A, it can be seen that with increased wetness or humidity, a chance that corrosion exists is more likely. However, a leveling of the humidity factor does occur at upper humidity limits. As shown in FIG. 6B, the potential corrosive activity increases with the increased chloride ion concentration. As shown in FIG. 6C, at the lower and upper regions of pH level, the potential for corrosive activity increases with a lesser potential for corrosive activity at a neutral pH. Further, as shown in FIG. 6D, the chances of corrosive activity increases with increased temperature up to some point where moisture will be baked out.

One skilled in the art will recognize that various other factors may contribute to the corrosive activity of different types of materials. Therefore, although the present sensed environmental factors are used to generate the exposure index in the illustrative embodiment shown and described with reference to FIGS. 2–5, other environmental factors may have an impact on the exposure index used or calculated with regard to a variety of materials.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative embodiments for sensing environmental factors and using such monitored factors for calculating exposure indexes as described herein may be implemented according to the present invention. Various modifications of the illustrative embodiments, various combinations of the various elements shown in the illustrative embodiments, as well as additional embodiments of the invention, will be apparent to persons skilled in the art upon reference to this description.

What is claimed is:

1. A monitoring method for monitoring an environment in which an object is located, the method comprising:
   monitoring one or more environmental factors associated with corrosion of materials in the environment; and
   calculating, in real-time, an exposure index representative of an actual cumulative exposure of the object to the one or more environmental factors as a function of a real-time measure of each individually monitored environmental factor.

2. The method of claim 1, wherein the method further comprises providing indication of the exposure index.

3. The method of claim 2, wherein providing indication of the exposure index comprises displaying the exposure index.

4. The method of claim 2, wherein the method further comprises recording data representative of the monitored environmental factors.

5. The method of claim 2, wherein the method further comprises continuously updating the exposure index.

6. The method of claim 1, wherein the method further comprises inspecting the object as a function of the exposure index.

7. The method of claim 1, wherein monitoring one or more environmental factors associated with corrosion of materials comprises sensing at least one of chloride ion concentration and pH in the environment.

8. The method of claim 7, wherein monitoring one or more environmental factors further comprises at least one of sensing humidity.

9. The method of claim 7, wherein monitoring one or more environmental factors comprises sensing temperature in the environment.

10. The method of claim 9, wherein the method further comprises correcting temperature dependence of one or more sensors used to monitor the environment based on the sensed temperature.

11. The method of claim 7, wherein monitoring one or more environmental factors comprises measuring free potential of a material positioned in the environment, wherein the object is formed at least in part of such a material.

12. The method of claim 11, wherein the method further comprises verifying the exposure index using the measured free potential of the material.

13. The method of claim 1, wherein calculating an exposure index comprises calculating the exposure index as a function of a real-time measure of at least one of chloride ion concentration and pH.

14. The method of claim 13, wherein calculating an exposure index further comprises calculating the exposure index as a function of a real-time measure of at least one of temperature and humidity.

15. The method of claim 13, wherein calculating the exposure index comprises calculating the exposure index as a function of a real-time measure of chloride ion concentration, pH, temperature and humidity.

16. A monitoring apparatus for monitoring an environment in which an object is located, comprising:
one or more sensors, wherein each sensor is operable to detect the presence of at least one environmental factor associated with corrosion of materials and provide real-time sensor signals representative of the detected environmental factor, and
a processing unit operable to receive the sensor signals generated by the one or more sensors, wherein the processing unit is operable to provide a real-time calculation of an exposure index representative of an actual cumulative exposure of the object to the at least one environmental factor as a function of the a real-time measure of each individually received sensor signals.

17. The apparatus of claim 16, wherein the apparatus further comprises an indication device indicating the exposure index.

18. The apparatus of claim 17, wherein indication device comprises a display.

19. The apparatus of claim 17, wherein the indication device continuously updates an indicated exposure index.

20. The apparatus of claim 16, wherein the apparatus further comprises memory to store data representative of at least one of the exposure index and data representative of the sensor signals.

21. The apparatus of claim 16, wherein the one or more sensors comprise at least one of a chloride ion concentration sensor and a pH sensor.

22. The apparatus of claim 21, wherein the one or more sensors further comprise at least one humidity sensor.

23. The apparatus of claim 21, wherein the one or more sensors further comprise a temperature sensor.

24. The apparatus of claim 16, wherein the one or more sensors further comprise a sensor to measure free potential of a sample material positioned in the environment, wherein the object is formed at least in part of such a material.

25. The apparatus of claim 16, wherein the one or more sensors comprise at least a chloride ion concentration sensor, a pH sensor, a temperature sensor, and a humidity sensor, and further wherein the processing unit provides the real-time calculation of the exposure index as a function of real-time sensor signals from the at least chloride ion concentration, pH, temperature and humidity.

26. The apparatus of claim 16, wherein the one or more sensors are removable from a sensor module housing such that one or more additional sensors can be substituted therefor.

27. The apparatus of claim 16, wherein the one or more sensors are associated with a module that is separate from a module containing the processing unit.

28. A monitoring method for monitoring an environment in which an object is located, the method comprising:
monitoring at least chloride ion concentration and pH in the environment; and
calculating, in real-time, an exposure index representative of an actual cumulative exposure of the object to a real-time measure of at least chloride ion concentration and pH.

29. The method of claim 28, wherein the method further comprises displaying the exposure index.

30. The method of claim 29, wherein the method further comprises continuously updating and displaying the exposure index.

31. The method of claim 28, wherein monitoring at least chloride ion concentration and pH further comprises sensing a real-time measure of humidity in the environment.

32. The method of claim 28, wherein monitoring at least chloride ion concentration and pH further comprises sensing a real-time measure of temperature in the environment.

* * * * *